(12) United States Patent
Zhou et al.

(10) Patent No.: US 10,648,959 B2
(45) Date of Patent: May 12, 2020

(54) BLACK PHOSPHORUS GAS SENSOR

(71) Applicant: University of Southern California, Los Angeles, CA (US)

(72) Inventors: Chongwu Zhou, Los Angeles, CA (US); Ahmad Abbas, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 15/587,914

(22) Filed: May 5, 2017

(65) Prior Publication Data
US 2017/0322166 A1  Nov. 9, 2017

Related U.S. Application Data (60) Provisional application No. 62/332,358, filed on May 5, 2016.

(51) Int. Cl.
*G01N 33/00* (2006.01)
*C23C 14/04* (2006.01)
(Continued)

(52) U.S. Cl.
CPC ..... *G01N 33/0037* (2013.01); *G01N 27/4141* (2013.01); *B23K 20/004* (2013.01);
(Continued)

(58) Field of Classification Search
CPC .............. B23K 20/004; B23K 2101/38; G01N 27/122; G01N 33/0037; Y02A 50/245
See application file for complete search history.

(56) References Cited

U.S. PATENT DOCUMENTS 9,620,627 B1 *  4/2017  Yeo ................... H01L 27/1203
2016/0077047 A1 *  3/2016  Khamis ............. G01N 27/4146
506/3

(Continued)

OTHER PUBLICATIONS

Abbas et al., "Black phosphorus gas sensors." ACS nano. May 6, 2015; 9(5):5618-24. (Year: 2015).*

(Continued)

*Primary Examiner* — Jennifer Wecker
(74) *Attorney, Agent, or Firm* — Michael Best & Friedrich LLP (57) ABSTRACT

The inventors experimentally demonstrated $NO_2$ gas sensing performance of multilayer black phosphorous (BP) field effect transistors. The BP sensors were sensitive to $NO_2$ concentration down to 5 ppb making them comparable in sensitivity to the best 2D material based sensors. Raman spectroscopy comparison revealed no apparent change in the spectra before and after exposure to $NO_2$, which shows that thick BP flakes can maintain their relative stability after sensing. Moreover, the BP device sensing performance fitted well with the Langmuir Isotherm for molecules adsorbed on a surface, which confirms charge transfer as the dominant mechanism for sensing. The systematic increase in conductance with increasing $NO_2$ concentrations suggests $NO_2$ molecules withdraw electrons and dope BP flakes with holes. These results lay the groundwork for BP to be applied to various sensing applications including chemical, gas, and bio-sensors.

17 Claims, 11 Drawing Sheets
(11 of 11 Drawing Sheet(s) Filed in Color)

(51) Int. Cl.

| | |
|---|---|
| *C23C 14/30* | (2006.01) |
| *H01L 29/40* | (2006.01) |
| *H01L 21/285* | (2006.01) |
| *G01N 27/414* | (2006.01) |
| *B23K 20/00* | (2006.01) |
| *H01J 37/305* | (2006.01) |
| *C23C 14/58* | (2006.01) |
| *B23K 101/38* | (2006.01) |
| *G01N 27/12* | (2006.01) |

(52) U.S. Cl.
CPC ........ *B23K 2101/38* (2018.08); *G01N 27/122* (2013.01); *Y02A 50/245* (2018.01)

(56) References Cited

U.S. PATENT DOCUMENTS

| | | | | |
|---|---|---|---|---|
| 2016/0190244 | A1* | 6/2016 | Lee ................... | H01L 29/78684 257/29 |
| 2016/0372553 | A1* | 12/2016 | Xiao ................... | H01L 29/1054 |
| 2017/0168327 | A1* | 6/2017 | Han ........................ | G02F 1/061 |
| 2017/0261465 | A1* | 9/2017 | Balijepalli, IV ... | G01N 27/4148 |

OTHER PUBLICATIONS

Abbas, A. N.; Liu, G.; Liu, B.; Zhang, L.; Liu, H.; Ohlberg, D.; Wu, W.; Zhou, C., Patterning, Characterization, and Chemical Sensing Applications of Graphene Nanoribbon Arrays Down to 5 nm Using Helium Ion Beam Lithography. ACS Nano 2014, 8, 1538-1546.
Buscema, M.; Groenendijk, D. J.; Blanter, S. I.; Steele, G. A.; van der Zant, H. S. J.; Castellanos-Gomez, A., Fast and Broadband Photoresponse of Few-Layer Black Phosphorus Field-Effect Transistors. Nano Lett. 2014, 14, 3347-3352.
Buscema, M.; Groenendijk, D. J.; Steele, G. A.; van der Zant, H. S. J.; Castellanos-Gomez, A., Photovoltaic effect in few-layer black phosphorus PN junctions defined by local electrostatic gating. Nat.Commun. 2014, 5.
Doganov, R. A.; O'Farrell, E. C. T.; Koenig, S. P.; Yeo, Y.; Ziletti, A.; Carvalho, A.; Campbell, D. K.; Coker, D. F.; Watanabe, K.; Taniguchi, T. et al. Accessing the transport properties of pristine few-layer black phosphorus by van der Waals passivation in inert atmosphere. arXiv 2014, arXiv:1412.1274.
Du, Y.; Liu, H.; Deng, Y.; Ye, P. D., Device Perspective for Black Phosphorus Field-Effect Transistors: Contact Resistance, Ambipolar Behavior, and Scaling. ACS Nano 2014, 8 (10), 10035-10042.
Engel, M.; Steiner, M.; Avouris, P., Black Phosphorus Photodetector for Multispectral, High-Resolution Imaging. Nano Lett. 2014, 14, 6414-6417.
Han, C. Q.; Yao, M. Y.; Bai, X. X.; Miao, L; Zhu, F.; Guan, D. D.; Wang, S.; Gao, C. L; Liu, C.; Qian, D. et al. Electronic structure of black phosphorus studied by angle-resolved photoemission spectroscopy. Phys. Rev. B 2014, 90, 085101.
He, Q.; Zeng, Z.; Yin, Z.; Li, H.; Wu, S.; Huang, X.; Zhang, H., Fabrication of Flexible MoS2 Thin-Film Transistor Arrays for Practical Gas-Sensing Applications. Small 2012, 8, 2994-2999.
Kamalakar, M. V.; Madhushankar, B. N.; Dankert, A.; Dash, S. P., Low Schottky Barrier Black Phosphorus Field-Effect Devices with Ferromagnetic Tunnel Contacts. Small, DOI:10.1002/smll. 201402900.
Koenig, S. P.; Doganov, R. A.; Schmidt, H.; Castro Neto, A. H.; Özyilmaz, B., Electric field effect in ultrathin black phosphorus. Appl. Phys. Lett. 2014, 104, 103106.
Kong, J.; Franklin, N. R.; Zhou, C.; Chapline, M. G.; Peng, S.; Cho, K.; Dai, H., Nanotube Molecular Wires as Chemical Sensors. Science 2000, 287, 622-625.
Köpf, M.; Eckstein, N.; Pfister, D.; Grotz, C.; Krüger, I.; Greiwe, M.; Hansen, T.; Kohlmann, H.; Nilges T., Access and in situ Growth of Phosphorene-Precursor Black Phosphorus, J. Cryst. Growth 2014, 405, 6-8.
Kou, L.; Frauenheim, T.; Chen, C., Phosphorene as a Superior Gas Sensor: Selective Adsorption and Distinct I-V Response. J. Phys. Chem. Lett. 2014, 5, 2675-2681.
Late, D. J.; Huang, Y.-K.; Liu, B.; Acharya, J.; Shirodkar, S. N.; Luo, J.; Yan, A.; Charles, D.; Waghmare, U. V.; Dravid, V. P. et al. Sensing Behavior of Atomically Thin-Layered MoS2 Transistors. ACS Nano 2013, 7, 4879-4891.
Li, H.; Yin, Z.; He, Q.; Li, H.; Huang, X.; Lu, G.; Farm D. W. H.; Tok, A. I. Y.; Zhang, Q.; Zhang, H., Fabrication of Single- and Multilayer MoS2 Film-Based Field-Effect Transistors for Sensing NO at Room Temperature. Small 2012, 8, 63-67.
Li, L.; Ye, G. J.; Tran, V.; Fei, R.; Chen, G.; Wang, H.; Wang, J.; Watanabe, K.; Taniguchi, T.; Yang, L. et al. Quantum Oscillations in Black Phosphorus Two-dimensional Electron Gas. arXiv 2014, arXiv:1411.6572.
Li, L.; Yu, Y.; Ye, G. J.; Ge, Q.; Ou, X.; Wu, H.; Feng, D.; Chen, X. H.; Zhang, Y., Black phosphorus field-effect transistors. Nat. Nanotechnol. 2014, 9, 372-377.
Liu, B.; Chen, L.; Liu, G.; Abbas, A. N.; Fathi, M.; Zhou, C., High-Performance Chemical Sensing Using Schottky-Contacted Chemical Vapor Deposition Grown Monolayer MoS2 Transistors. ACS Nano 2014, 8, 5304-5314.
Liu, H.; Neal, A. T.; Zhu, Z.; Luo, Z.; Xu, X.; Tománek, D.; Ye, P. D., Phosphorene: An Unexplored 2D Semiconductor with a High Hole Mobility. ACS Nano 2014, 8, 4033-4041.
Low, T.; Rodin, A. S.; Carvalho, A.; Jiang, Y.; Wang, H.; Xia, F.; Castro Neto, A. H., Tunable optical properties of multilayer black phosphorus thin films. Phys. Rev. B 2014, 90, 075434.
Perkins, F. K.; Friedman, A. L.; Cobas, E.; Campbell, P. M.; Jernigan, G. G.; Jonker, B. T., Chemical Vapor Sensing with Monolayer MoS2. Nano Lett. 2013, 13, 668-673.
Qi, P.; Vermesh, O.; Grecu, M.; Javey, A.; Wang, Q.; Dai, H.; Peng, S.; Cho, K. J., Toward Large Arrays of Multiplex Functionalized Carbon Nanotube Sensors for Highly Sensitive and Selective Molecular Detection. Nano Lett. 2003, 3, 347-351.
Schedin, F.; Geim, A. K.; Morozov, S. V.; Hill, E. W.; Blake, P.; Katsnelson, M. I.; Novoselov, K. S., Detection of individual gas molecules adsorbed on graphene. Nat. Mater. 2007, 6, 652-655.
Takahashi, T.; Gunasekara, N.; Ohsawa, H.; Ishii, H.; Kinoshita, T.; Suzuki, S.; Sagawa; T.; Kato, H.; Miyahara, T.; Shirotani, I., Angle-resolved photoemission study of black phosphorus: Interlayer energy dispersion. Phys. Rev. B 1986, 33, 4324-4326.
U.S. Department of Environmental Protection Agency. http://www.epa.gov/Air/Nitrogenoxides/.
Wang, H.; Wang, X.; Xia, F.; Wang, L.; Jiang, H.; Xia, Q.; Chin, M. L.; Dubey, M.; Han,S.-j., Black Phosphorus Radio-Frequency Transistors. Nano Lett. 2014, 14, 6424-6429.
Wood, J. D.; Wells, S. A.; Jariwala, D.; Chen, K.-S.; Cho, E.; Sangwan, V. K.; Liu, X.; Lauhon, L. J.; Marks, T. J.; Hersam, M. C., Effective Passivation of Exfoliated Black Phosphorus Transistors against Ambient Degradation. Nano Lett. 2014, 14, 6964-6970.
Xi, L.; Rahbarihagh, Y.; Hwang, J. C. M.; Han, L.; Yuchen, D.; Ye, P. D., Temporal and Thermal Stability of Al2O3-Passivated Phosphorene MOSFETs. IEEE Electron Device Lett. 2014, 35, 1314-1316.
Xia, F.; Wang H.; Jia, Y.; Rediscovering black phosorus as an anisotropic layered material for optoelectronics and electronics. Nat. Commun. 2014, 5.
Youngblood, N.; Chen, C.; Koester, S. J.; Li, M., Waveguide-integrated black phosphorus photodetector with high responsivity and low dark current. Nat. Photonics 2015, doi:10.1038/nphoton. 2015.23.
Yu, W. J.; Li, Z.; Zhou, H.; Chen, Y.; Wang, Y.; Huang, Y.; Duan, X., Vertically stacked multi-heterostructures of layered materials for logic transistors and complementary inverters. Nat. Mater. 2012, 12, 246-252.
Yuan, H.; Liu, X.; Afshinmanesh, F.; Li, W.; Xu, G.; Sun, J.; Lian, B.; Ye, G.; Hikita, Y.; Shen, Z. et al. Broadband Linear-Dichroic Photodetector in a Black Phosphorus Vertical p-n. Junction. arXiv 2014, arXiv:1409.4729.
Zhang, D.; Liu, Z.; Li, C.; Tang, T.; Liu, X.; Han, S.; Lei, B.; Zhou, C., Detection of NO2 down to ppb Levels Using Individual and Multiple In2O3 Nanowire Devices. Nano Lett. 2004, 4, 1919-1924.

(56) References Cited

OTHER PUBLICATIONS

Zhang X.; Xie, H.; Liu, Z.; Tan, C.; Luo, Z.; Li, H.; Lin, J.; Sun, L.; Chen, W.; Xu, Z. et al. Black Phosphorus Quantum Dots. Angew. Chem., Int. Ed., DOI: 10.1002/anie.201409400.

Zhang Y.; Kolmakov, A.; Chretien, S.; Metiu, H.; Moskovits, M., Control of Catalytic Reactions at the Surface of a Metal Oxide Nanowire by Manipulating Electron Density Inside It. Nano Lett. 2004, 4, 403-407.

Ziletti A.; Carvalho, A.; Campbell, D. K.; Coker, D. F.; Castro Neto, A. H., Oxygen Defects in Phosphorene. Phys. Rev. Lett. 2015, 114, 046801.

Zou, X.; Wang, J.; Liu, X.; Wang, C.; Jiang, Y.; Wang, Y.; Xiao, X.; Ho, J. C.; Li, J.; Jiang, C. et al. Rational Design of Sub-Parts per Million Specific Gas Sensors Array Based on Metal Nanoparticles Decorated Nanowire Enhancement-Mode Transistors. Nano Lett. 2013, 13, 3287-3292.

Abbas et al., "Black phosphorus gas sensors." ACS nano. May 6, 2015; 9(5):5618-24.

\* cited by examiner

BLACK PHOSPHORUS GAS SENSOR

CROSS-REFERENCE TO RELATED APPLICATION(S)

This application claims the benefit of U.S. Patent Application No. 62/332,358; filed on May 5, 2016; entitled "BLACK PHOSPHORUS GAS SENSORS."

STATEMENT REGARDING FEDERALLY SPONSORED RESEARCH OR DEVELOPMENT

This invention was made with government support under Grant Number N00014-11-1-0880 awarded by the Office of Naval Research (ONR). The government has certain rights in this invention.

BACKGROUND

The utilization of black phosphorus and its monolayer (phosphorene) and few-layers in field-effect transistors has attracted a lot of attention to this elemental two-dimensional material. Various studies on optimization of black phosphorus field-effect transistors, PN junctions, photodetectors, and other applications have been demonstrated. There is no experimental verification of chemical sensing based on black phosphorus devices.

One or more of the following references may be referred to in this disclosure. The references are incorporated herein by reference.

Li, L.; Yu, Y.; Ye, G. J.; Ge, Q.; Ou, X.; Wu, H.; Feng, D.; Chen, X. H.; Zhang, Y., Black phosphorus field-effect transistors. *Nat. Nanotechnol.* 2014, 9, 372-377.

Xia, F.; Wang, H.; Jia, Y., Rediscovering black phosphorus as an anisotropic layered material for optoelectronics and electronics. *Nat. Commun.* 2014, 5.

Liu, H.; Neal, A. T.; Zhu, Z.; Luo, Z.; Xu, X.; Tomànek, D.; Ye, P. D., Phosphorene: An Unexplored 2D Semiconductor with a High Hole Mobility. *ACS Nano* 2014, 8, 4033-4041.

Koenig, S. P.; Doganov, R. A.; Schmidt, H.; Castro Neto, A. H.; Özyilmaz, B., Electric field effect in ultrathin black phosphorus. *Appl. Phys. Lett.* 2014, 104, 103106.

Wang, H.; Wang, X.; Xia, F.; Wang, L.; Jiang, H.; Xia, Q.; Chin, M. L.; Dubey, M.; Han, S.-j., Black Phosphorus Radio-Frequency Transistors. *Nano Lett.* 2014, 14, 6424-6429.

Zhang, X.; Xie, H.; Liu, Z.; Tan, C.; Luo, Z.; Li, H.; Lin, J.; Sun, L.; Chen, W.; Xu, Z. et al. Black Phosphorus Quantum Dots. *Angew. Chem., Int. Ed.*, DOI: 10.1002/anie.201409400.

Kamalakar, M. V.; Madhushankar, B. N.; Dankert, A.; Dash, S. P., Low Schottky Barrier Black Phosphorus Field-Effect Devices with Ferromagnetic Tunnel Contacts. *Small*, DOI:10.1002/smll.201402900.

Li, L.; Ye, G. J.; Tran, V.; Fei, R.; Chen, G.; Wang, H.; Wang, J.; Watanabe, K.; Taniguchi, T.; Yang, L. et al. Quantum Oscillations in Black Phosphorus Two-dimensional Electron Gas. *arXiv* 2014, *arXiv:* 1411.6572.

Buscema, M.; Groenendijk, D. J.; Steele, G. A.; van der Zant, H. S. J.; Castellanos-Gomez, A., Photovoltaic effect in few-layer black phosphorus PN junctions defined by local electrostatic gating. *Nat. Commun.* 2014, 5.

Du, Y.; Liu, H.; Deng, Y.; Ye, P. D., Device Perspective for Black Phosphorus Field-Effect Transistors: Contact Resistance, Ambipolar Behavior, and Scaling. *ACS Nano* 2014, 8 (10), 10035-10042.

Engel, M.; Steiner, M.; Avouris, P., Black Phosphorus Photodetector for Multispectral, High-Resolution Imaging. *Nano Lett.* 2014, 14, 6414-6417.

Buscema, M.; Groenendijk, D. J.; Blanter, S. I.; Steele, G. A.; van der Zant, H. S. J.; Castellanos-Gomez, A., Fast and Broadband Photoresponse of Few-Layer Black Phosphorus Field-Effect Transistors. *Nano Lett.* 2014, 14, 3347-3352.

Youngblood, N.; Chen, C.; Koester, S. J.; Li, M., Waveguide-integrated black phosphorus photodetector with high responsivity and low dark current. *Nat. Photonics* 2015, doi: 10.1038/nphoton.2015.23.

Yuan, H.; Liu, X.; Afshinmanesh, F.; Li, W.; Xu, G.; Sun, J.; Lian, B.; Ye, G.; Hikita, Y.; Shen, Z. et al. Broadband Linear-Dichroic Photodetector in a Black Phosphorus Vertical p-n Junction. *arXiv* 2014, *arXiv:* 1409.4729.

Wood, J. D.; Wells, S. A.; Jariwala, D.; Chen, K.-S.; Cho, E.; Sangwan, V. K.; Liu, X.; Lauhon, L. J.; Marks, T. J.; Hersam, M. C., Effective Passivation of Exfoliated Black Phosphorus Transistors against Ambient Degradation. *Nano Lett.* 2014, 14, 6964-6970.

Ziletti, A.; Carvalho, A.; Campbell, D. K.; Coker, D. F.; Castro Neto, A. H., Oxygen Defects in Phosphorene. *Phys. Rev. Lett.* 2015, 114, 046801.

Kou, L.; Frauenheim, T.; Chen, C., Phosphorene as a Superior Gas Sensor: Selective Adsorption and Distinct I-V Response. *J. Phys. Chem. Lett.* 2014, 5, 2675-2681.

Kong, J.; Franklin, N. R.; Zhou, C.; Chapline, M. G.; Peng, S.; Cho, K.; Dai, H., Nanotube Molecular Wires as Chemical Sensors. *Science* 2000, 287, 622-625.

Qi, P.; Vermesh, O.; Grecu, M.; Javey, A.; Wang, Q.; Dai, H.; Peng, S.; Cho, K. J., Toward Large Arrays of Multiplex Functionalized Carbon Nanotube Sensors for Highly Sensitive and Selective Molecular Detection. *Nano Lett.* 2003, 3, 347-351.

Zhang, D.; Liu, Z.; Li, C.; Tang, T.; Liu, X.; Han, S.; Lei, B.; Zhou, C., Detection of NO2 down to ppb Levels Using Individual and Multiple In2O3 Nanowire Devices. *Nano Lett.* 2004, 4, 1919-1924.

Zou, X.; Wang, J.; Liu, X.; Wang, C.; Jiang, Y.; Wang, Y.; Xiao, X.; Ho, J. C.; Li, J.; Jiang, C. et al. Rational Design of Sub-Parts per Million Specific Gas Sensors Array Based on Metal Nanoparticles Decorated Nanowire Enhancement-Mode Transistors. *Nano Lett.* 2013, 13, 3287-3292.

Schedin, F.; Geim, A. K.; Morozov, S. V.; Hill, E. W.; Blake, P.; Katsnelson, M. I.; Novoselov, K. S., Detection of individual gas molecules adsorbed on graphene. *Nat. Mater.* 2007, 6, 652-655.

Abbas, A. N.; Liu, G.; Liu, B.; Zhang, L.; Liu, H.; Ohlberg, D.; Wu, W.; Zhou, C., Patterning, Characterization, and Chemical Sensing Applications of Graphene Nanoribbon Arrays Down to 5 nm Using Helium Ion Beam Lithography. *ACS Nano* 2014, 8, 1538-1546.

Li, H.; Yin, Z.; He, Q.; Li, H.; Huang, X.; Lu, G.; Fam, D. W. H.; Tok, A. I. Y.; Zhang, Q.; Zhang, H., Fabrication of Single- and Multilayer MoS2 Film-Based Field-Effect Transistors for Sensing NO at Room Temperature. *Small* 2012, 8, 63-67.

He, Q.; Zeng, Z.; Yin, Z.; Li, H.; Wu, S.; Huang, X.; Zhang, H., Fabrication of Flexible MoS2 Thin-Film Transistor Arrays for Practical Gas-Sensing Applications. *Small* 2012, 8, 2994-2999.

Late, D. J.; Huang, Y.-K.; Liu, B.; Acharya, J.; Shirodkar, S. N.; Luo, J.; Yan, A.; Charles, D.; Waghmare, U. V.; Dravid, V. P. et al. Sensing Behavior of Atomically Thin-Layered MoS2 Transistors. *ACS Nano* 2013, 7, 4879-4891.

Perkins, F. K.; Friedman, A. L.; Cobas, E.; Campbell, P. M.; Jernigan, G. G.; Jonker, B. T., Chemical Vapor Sensing with Monolayer MoS2. *Nano Lett.* 2013, 13, 668-673.

Liu, B.; Chen, L.; Liu, G.; Abbas, A. N.; Fathi, M.; Zhou, C., High-Performance Chemical Sensing Using Schottky-Contacted Chemical Vapor Deposition Grown Monolayer MoS2 Transistors. *ACS Nano* 2014, 8, 5304-5314.

U.S. Department of Environmental Protection Agency. http://www.epa.gov/Air/Nitrogenoxides/.

Xi, L.; Rahbarihagh, Y.; Hwang, J. C. M.; Han, L.; Yuchen, D.; Ye, P. D., Temporal and Thermal Stability of Al2O3-Passivated Phosphorene MOSFETs. *IEEE Electron Device Lett.* 2014, 35, 1314-1316.

Doganov, R. A.; O'Farrell, E. C. T.; Koenig, S. P.; Yeo, Y.; Ziletti, A.; Carvalho, A.; Campbell, D. K.; Coker, D. F.; Watanabe, K.; Taniguchi, T. et al. Accessing the transport properties of pristine few-layer black phosphorus by van der Waals passivation in inert atmosphere. *arXiv* 2014, arXiv: 1412.1274.

Zhang, Y.; Kolmakov, A.; Chretien, S.; Metiu, H.; Moskovits, M., Control of Catalytic Reactions at the Surface of a Metal Oxide Nanowire by Manipulating Electron Density Inside It. *Nano Lett.* 2004, 4, 403-407.

Low, T.; Rodin, A. S.; Carvalho, A.; Jiang, Y.; Wang, H.; Xia, F.; Castro Neto, A. H., Tunable optical properties of multilayer black phosphorus thin films. *Phys. Rev. B* 2014, 90, 075434.

Takahashi, T.; Gunasekara, N.; Ohsawa, H.; Ishii, H.; Kinoshita, T.; Suzuki, S.; Sagawa; T; Kato, H.; Miyahara, T.; Shirotani, I., Angle-resolved photoemission study of black phosphorus: Interlayer energy dispersion. *Phys. Rev. B* 1986, 33, 4324-4326.

Han, C. Q.; Yao, M. Y.; Bai, X. X.; Miao, L.; Zhu, F.; Guan, D. D.; Wang, S.; Gao, C. L.; Liu, C.; Qian, D. et al. Electronic structure of black phosphorus studied by angle-resolved photoemission spectroscopy. *Phys. Rev. B* 2014, 90, 085101.

Yu, W. J.; Li, Z.; Zhou, H.; Chen, Y.; Wang, Y.; Huang, Y.; Duan, X., Vertically stacked multiheterostructures of layered materials for logic transistors and complementary inverters. *Nat. Mater.* 2012, 12, 246-252.

Köpf, M.; Eckstein, N.; Pfister, D.; Grotz, C.; Krüger, I.; Greiwe, M.; Hansen, T.; Kohlmann, H.; Nilges T., Access and in situ Growth of Phosphorene-Precursor Black Phosphorus, *J. Cryst. Growth* 2014, 405, 6-8.

SUMMARY

Disclosed herein is chemical sensing of nitrogen dioxide ($NO_2$) using field-effect transistors based on multilayer black phosphorus. Black phosphorus sensors exhibited increased conduction upon $NO_2$ exposure and excellent sensitivity for detection of $NO_2$ down to 5 parts per billion (ppb). Moreover, when the multilayer black phosphorus field-effect transistor was exposed to $NO_2$ concentrations of 5, 10, 20, and 40 ppb, the transistor's relative conduction change followed the Langmuir isotherm for molecules adsorbed on a surface. Additionally, based on an exponential conductance change, the rate constants for adsorption and desorption of $NO_2$ on black phosphorus were extracted for different $NO_2$ concentrations, and they were in the range of 130-840 sec. These results shed light on electronic and sensing characteristics of black phosphorus.

In one embodiment, the invention provides a black phosphorus gas sensor having repeatable sensing performance. The sensor includes a substrate, a black phosphorus flake supported by the substrate, and a plurality of electrical contacts supported by the substrate and coupled to the black phosphorus flake. The black phosphorus flake can have a thickness greater than 15 nanometers.

In another embodiment, the invention provides a method of sensing a with the black phosphorus gas sensor. The method includes providing the black phosphorus gas sensor at a location, exposing the black phosphorus gas sensor to a gas, and conducting a current from a first electrode to a second electrode of the plurality of electrodes and through the black phosphorus flake. The conduction is based on the concentration of the gas.

Also disclosed is a method of manufacturing the black phosphorus gas sensor.

Other aspects of the invention will become apparent by consideration of the detailed description and accompanying drawings.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Recently, the rediscovery of black phosphorus (BP) as a single-element, two-dimensional (2D) layered material has sparked the interest of scientists in various fields. Electronic and optical properties showed great promise for using BP in numerous applications. The field-effect transistor (FET) of few-layer BP exhibited high charge mobility, anisotropic transport behavior, high operating frequencies, and relatively high current on/off ratios, making BP a potential candidate for future electronics. The recently reported device optimization techniques of BP FETs have yielded transistors with even better performance (e.g. higher mobility and lower contact resistance). In Addition, optical applications including photovoltaics (PV), photodetectors, and imaging devices were created using BP FETs with different device structures. Moreover, passivation and stability of black phosphorus has also been studied. On the other hand, other applications such as chemical sensing of BP remain only theoretically explored.

Chemical sensing using various nanomaterials is a promising application, due to the inherent large surface-to-volume ratios. A variety of nanomaterials including carbon nanotubes, nanowires, and graphene were extensively studied for chemical and gas sensing applications. In the 2D family, both exfoliated and chemical-vapor-deposited (CVD) $MoS_2$ with various thicknesses were used for chemical sensing. The sensitivity of these sensors varied significantly depending on flake thickness, metal contacts, method of synthesis, and other factors. For example, chemical sensitivity of $MoS_2$ FETs to nitrogen dioxide ($NO_2$) varied from a few hundred parts per million (ppm) in exfoliated samples to a few parts per billion (ppb) in monolayer CVD samples.

$NO_2$ is a common gas produced as a byproduct in industrial plants and vehicles. According to the U.S. Department of Environmental Protection Agency (EPA), exposure to $NO_2$ concentrations larger than 53 ppb can cause possible health problems. Consequently, detection of this gas with sensitivities better than the aforementioned limit has value. BP, being a 2D material, is predicted to be sensitive to various chemicals with comparable or better sensitivities than $MoS_2$ and graphene because the adsorption energies, of molecules such as $NO_2$ and NO are larger with BP than with graphene and $MoS_2$. It is believed that there is yet no systematic experimental verification of gas and/or chemical sensing of BP FETs.

The chemical sensing performance of multilayer BP FET to $NO_2$ gas is disclosed herein. Specifically, the stability of BP sensors by Raman spectroscopy of flakes before and after sensing is studied, which revealed no difference in the spectra, indicating the multilayer BP was stable for the timeframe, and repeated sensing. In one implementation, the BP FET was exposed to varying concentrations of $NO_2$ and the relative conductance change in the device was monitored. The BP FET showed a systematic increase in conductance with varying concentrations, indicative of hole doping charge transfer caused by $NO_2$ molecules. The multilayer BP sensor exhibited a clear conductance change to $NO_2$ concentrations as low as 5 ppb comparing favorably with the performance of almost all other 2D sensors including monolayer $MoS_2$. Moreover, the device showed a good recovery to the original conductance after flushing the device with argon, suggesting a reversible adsorption and desorption of $NO_2$. The relative conductance change fitted fairly well with Langmuir Isotherm for molecular adsorption on a surface. This implies that $NO_2$ molecular adsorption via site binding and charge transfer are the sensing mechanisms for the some BP devices. Additionally, the adsorption and desorption rates of $NO_2$ molecules on the BP surface was studied and the rate constants for various $NO_2$ concentrations were derived. The drain current vs. drain voltage ($I_d$-$V_d$) and drain current vs. gate voltage ($I_d$-$V_g$) of the BP FET under varying concentrations of $NO_2$ was examined, which showed a systematic increase in conductance and good consistency with Langmuir Isotherm.

Figure 1:
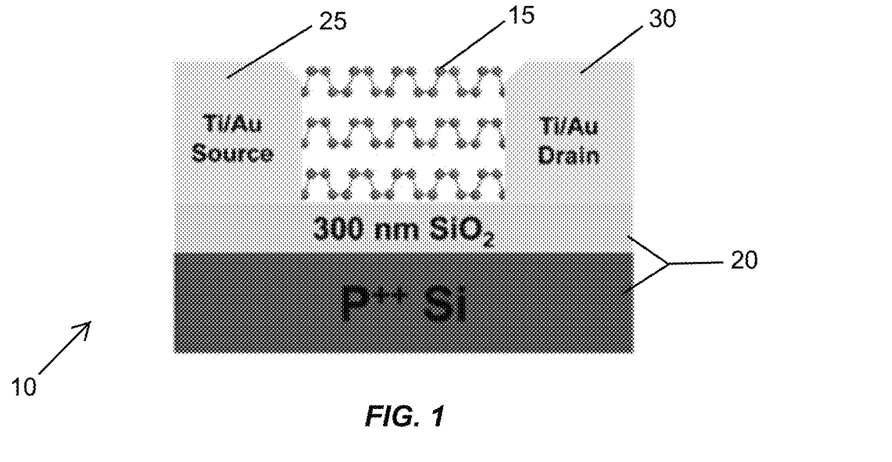
FIG. 1 depicts a scheme of a multilayer BP FET.
Figure 2:
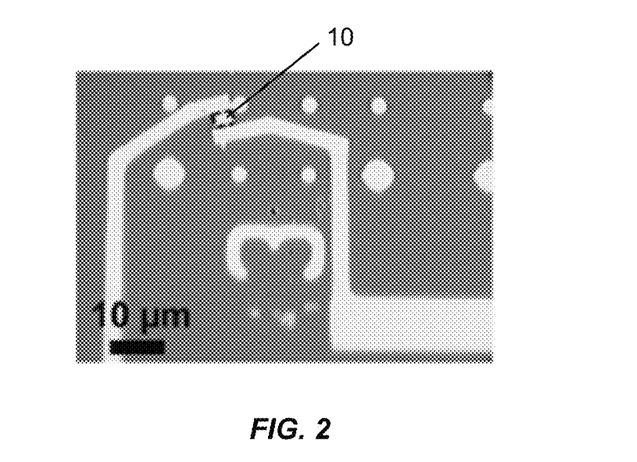
FIG. 2 depicts an optical image of the multilayer BP flake between two Ti/Au electrodes.
Figure 3:
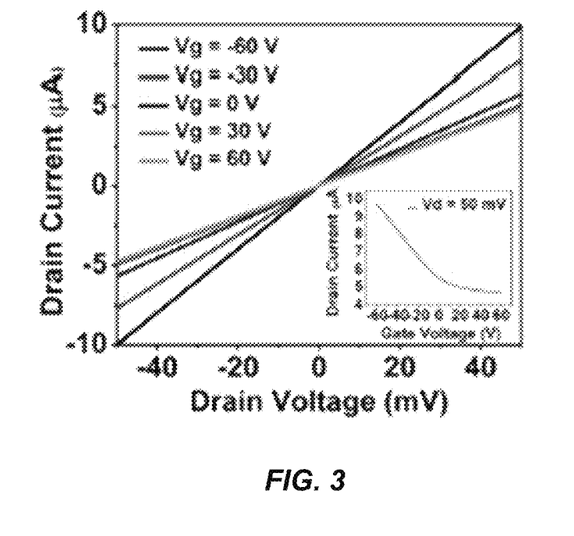
FIG. 3 depicts the $I_d$-$V_d$ curves of the device at different back gate voltages and an inset of an $I_d$-$V_g$ curve.
Figure 4:
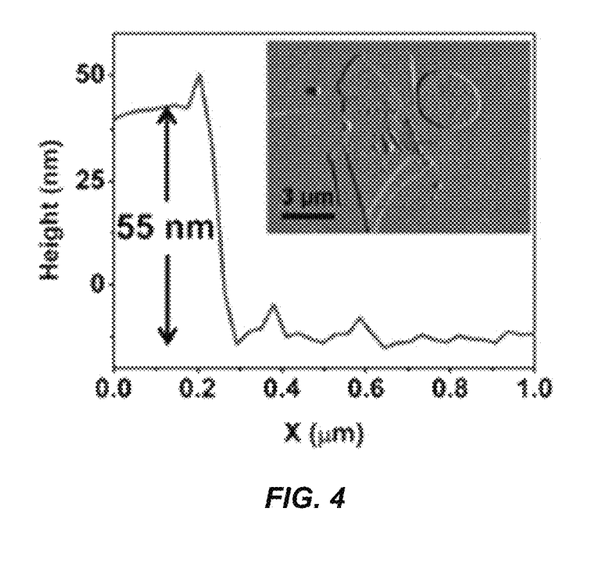
FIG. 4 shows an atomic force microscope (AFM) height profile of the BP flake revealing a height of ~55 nm.
Figure 5:
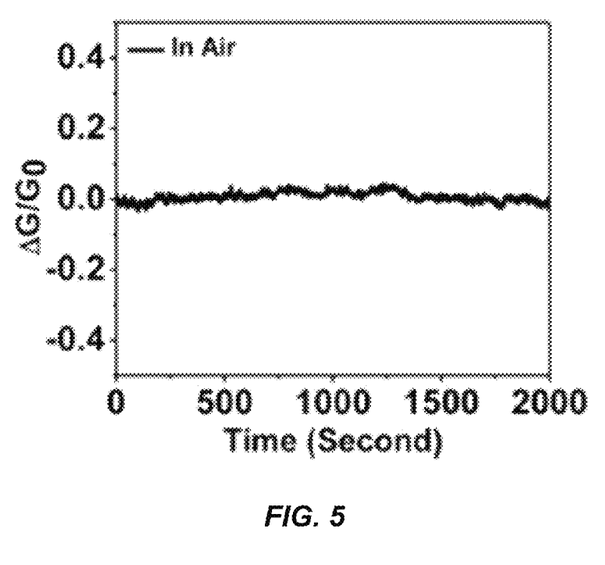
FIG. 5 depicts a bias stress test of a BP multilayer flake in air.
Figure 6:
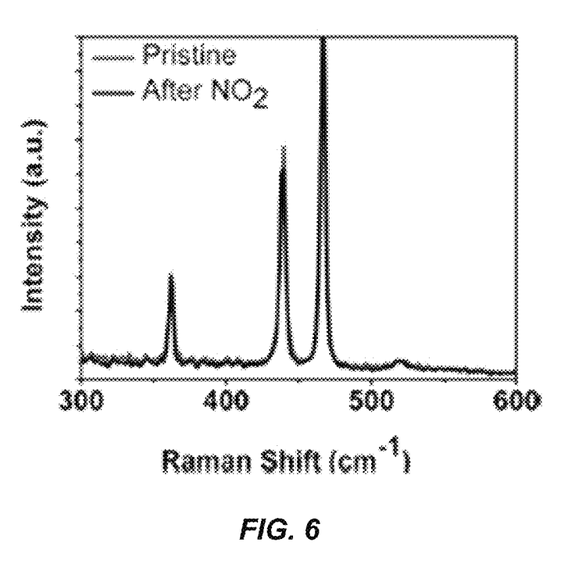
FIG. 6 depicts a Raman spectroscopy taken on a multilayer BP flake before (red) and after (black) exposure to 800 ppb $NO_2$ for ~30 minutes.
Figure 15:
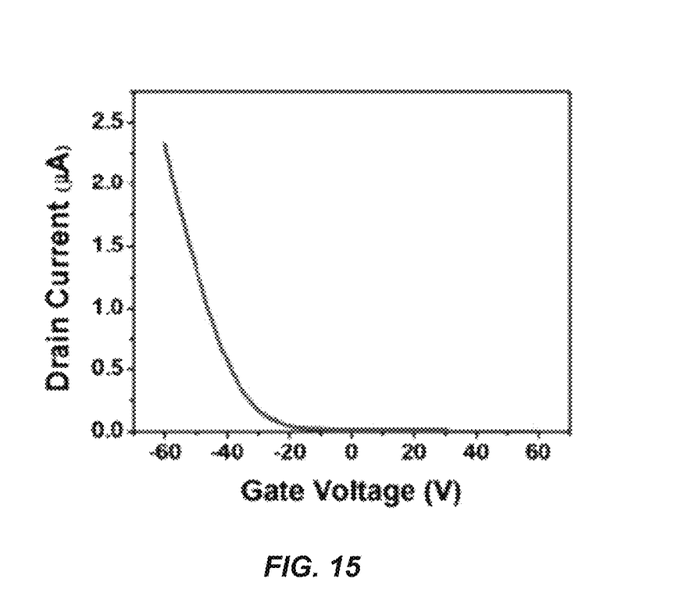
FIG. 15 depicts the $I_d$-$V_g$ curve of a ~10 nm flake BP FET under a 50 mV $V_d$.
Figure 16:
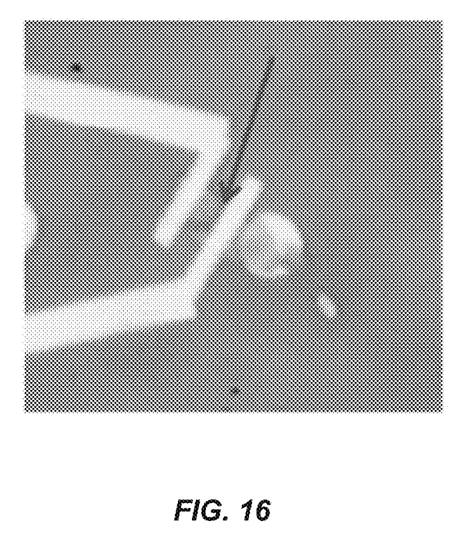
FIG. 16 depicts the optical image of the device in FIG. 15 after repeated measurements in air.
Figure 17:
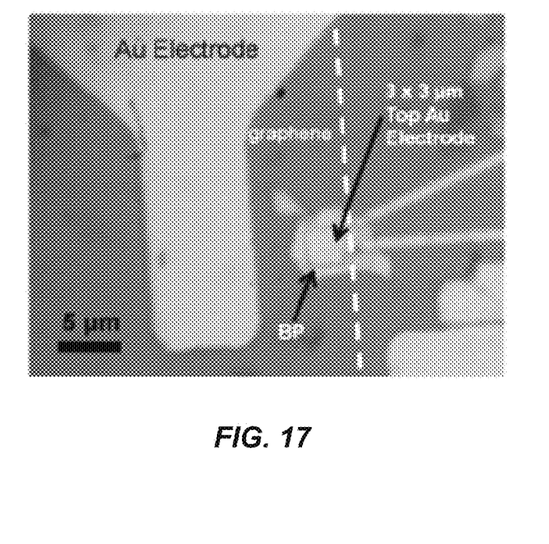
FIG. 17 depicts an optical microscope image of a vertical FET comprised of a bottom monolayer CVD graphene electrode/BP/top (Ti/Au) electrode with a $P^{++}$ Si/300 nm $SiO_2$ back gated structure.
Figure 18:
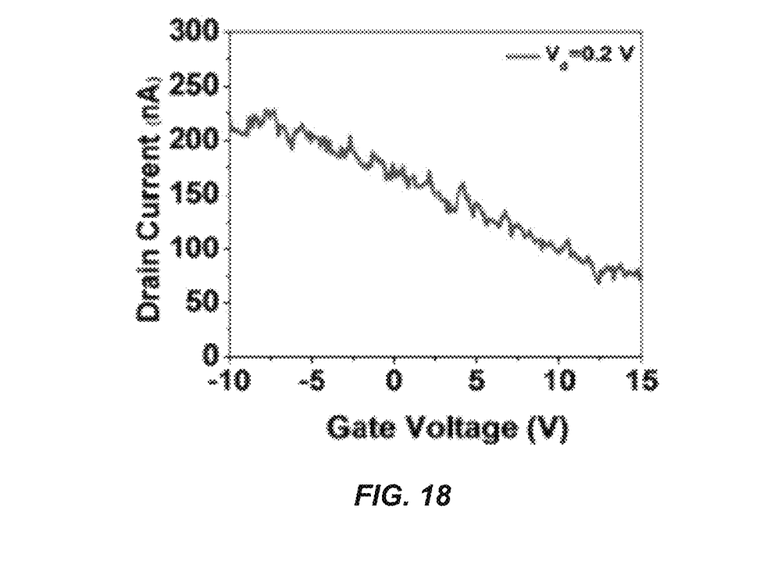
FIG. 18 depicts the $I_d$-$V_G$ curve for the device in FIG. 17.

FIG. 1 shows a schematic of a multilayer BP FET 10 used for chemical sensing (may also be referred to herein as BP sensor 10). First, chemically synthesized BP flakes 15 were exfoliated, using a scotch tape, on a $P^{2+}$ Si/300 nm $SiO_2$ substrate 20 and subsequently patterned with contact metals (0.5 nm Ti/50 nm Au) as source 25 and drain 30 electrodes. In the back gate configuration, the $P^{2+}$ Si acts as a back gate and the 300 nm $SiO_2$ is the dielectric. FIG. 2 reveals an optical image showing the multilayer BP FET 10 used for $NO_2$ sensing. The $I_d$-$V_d$ curves of the device at different back gate voltages and an inset of an $I_d$-$V_g$ curve are shown in FIG. 3. The linearity of $I_d$-$V_d$ curves suggests Ohmic contacts between Au and multilayer BP. The nondepletable performance of the multilayer BP flake is due to the electric field screening effect in thick BP flakes. FIG. 4 shows an atomic force microscope (AFM) image of the multilayer BP sensor 10 and a height profile revealing a thickness of ~55 nm. The use of thick BP flakes may stabilize the BP sensor 10 and it was recently applied to other applications of BP such as imaging. Generally, a stable performance over the sensing experiment is required for reliable sensing. Specifically, BP FETs 10, using relatively thin BP, have displayed degradation in performance under ambient conditions due to the oxidation of phosphorus. Recently, several solutions were developed to encapsulate and passivate BP FETs 10 to maintain good performance under ambient conditions. See Wood et al., Xi et al., and Doganov et al. These methods are not applicable for sensing applications since direct exposure of the device active material to the chemical is required. Thick BP flakes were used in the sensing experiments described herein to enhance the stability of the device and reduce degradation under exposure to $NO_2$. In one implementation, the thick BP flakes have a thickness greater than 50 nm. Although thinner BP flakes (e.g., BP flakes smaller than 15 nm) may theoretically offer better sensing performance because of the larger surface-to-volume ratio and larger bandgaps (i.e., reduced charge density), thinner flakes maybe more affected by oxidation than thicker flakes. On the basis of the inventors' experiments, the inventors observed that continuous electrical measurements of thin BP flakes in air made the BP FET fail (see FIGS. 15 and 16). On the other hand, a bias stress test of a thick BP flake in air showed relatively stable performance with a conductance variation less than 4% (see FIG. 5). To isolate the effect of $NO_2$ on BP from other species, such as oxygen and water vapor, the sensing experiments were carried out in an argon environment (i.e. $NO_2$ diluted in argon). Nonetheless, the relatively stable conductance value in air is promising for more practical sensing applications. To further investigate the effect of $NO_2$ exposure on BP flakes, the inventors compared the Raman spectrum of BP flakes before and after exposure to $NO_2$. Due to the anisotropic nature of BP, care was taken to keep the laser polarization, for a specific flake, in the same direction in all Raman measurements. FIG. 6 shows a Raman spectroscopy taken on a multilayer BP flake before and after exposure to 800 ppb $NO_2$ for ~30 min. It can be seen that all peaks associated with BP ($A^1_g$ at ~362 cm$^{-1}$, $A^2_g$ at ~466 cm$^{-1}$, and $B_{2g}$ at ~440 cm$-1$) remain in the same positions and show similar relative peak intensity ratios before and after exposure. This suggests minimal chemical degradation of multilayer BP flakes used in the experiments during $NO_2$ exposure.

The $NO_2$ sensing experiment starts by loading the device in a gas chamber while flushing the system with argon for a time period (e.g., 10 mins). Afterwards, the $NO_2$ gas is diluted with argon to produce various concentrations and the BP sensor 10 is subsequently exposed to the desired concentration. After the exposure to a certain $NO_2$ concentration, the system is flushed with argon for 300 seconds to partially recover BP sensor 10 and to observe a conductance change opposite to the $NO_2$ exposure period. Finally, when the BP sensor 10 is exposed to all desired concentrations, the gas chamber is flushed with argon until the device recovers to the original conductance value.

Figure 7:
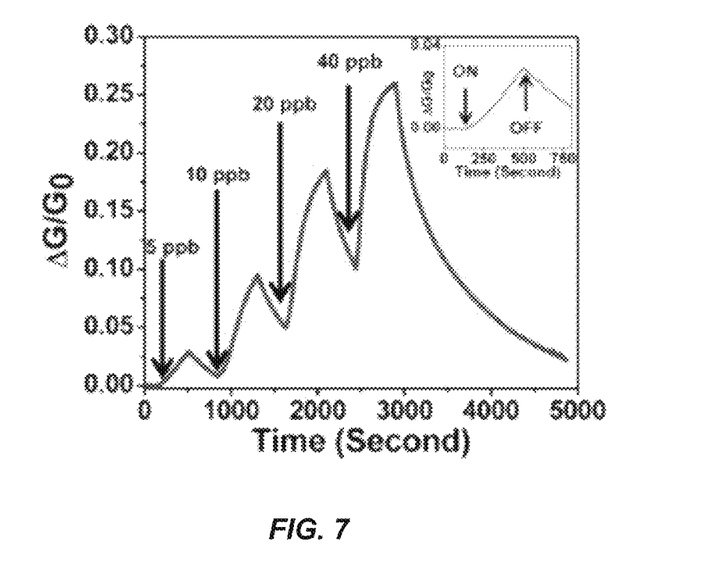
FIG. 7 depicts the relative conductance change ($\Delta G/G_0$) vs time in seconds for a multilayer BP sensor showing a sensitivity to $NO_2$ concentrations (5-40 ppb). The inset of FIG. 7 depicts a zoomed in image of a 5 ppb $NO_2$ exposure response with identification of points in time where the $NO_2$ gas is switched on and off.
Figure 8:
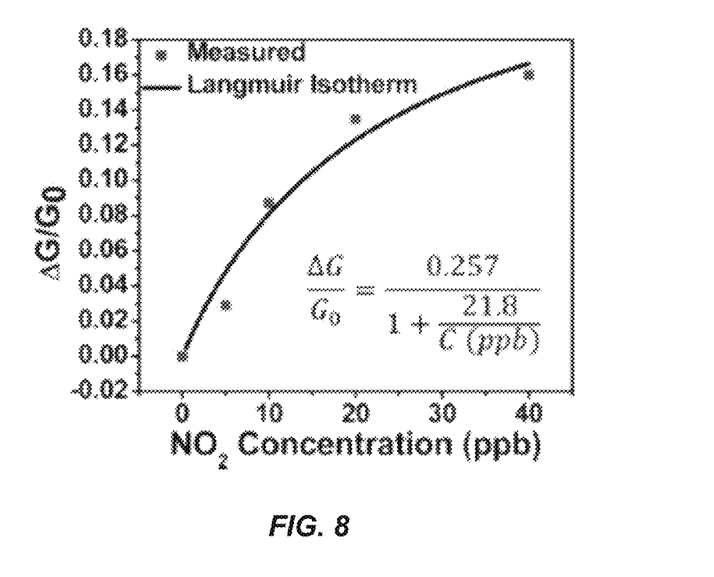
FIG. 8 depicts the measured $\Delta G/G_0$ plotted vs. $NO_2$ gas concentration.

FIGS. 7 and 8 show the results from the above-described sensing experiment. In FIG. 7, the relative conductance change $\Delta G/G_0$ is plotted vs. time (where $\Delta G=G-G_0$, G is the instantaneous conductance of the device, and $G_0$ is the conductance of the device before exposure to $NO_2$). The inset of FIG. 7 illustrates the point in time where the BP sensor 10 is exposed to 5 ppb $NO_2$ concentration (i.e., ON) and when the BP sensor 10 is flushed with argon (i.e., OFF). It can be clearly observed that the BP sensor 10 responds to $NO_2$ concentrations down to 5 ppb evident by a conductance change of 2.9%. The relatively high sensitivity to $NO_2$ for multilayer BP is very interesting and may be further improved by reducing the layer number and increasing the surface-to-volume ratio. Additionally, it can be seen that the conductance change is monotonic and systematically increases as the concentration increases from 5 ppb to 40 ppb. After exposure to all $NO_2$ concentrations, the BP sensor 10 recovers while being flushed with argon in a period of ~35 mins and can be used again for another round of sensing (FIG. 7). In FIG. 8, the measured $\Delta G/G_0$ is plotted vs. $NO_2$ gas concentration. $\Delta G/G_0$ is extracted by taking the difference of the ON and OFF values (FIG. 7 inset) for each concentration. The data points in FIG. 8 fit with Langmuir Isotherm for molecules adsorbed on a surface with equation:

$$\frac{\Delta G}{G_0} = \frac{0.257}{1+\frac{21.8}{C(ppb)}}, \quad \text{(Eq. 1)}$$

Figure 21:
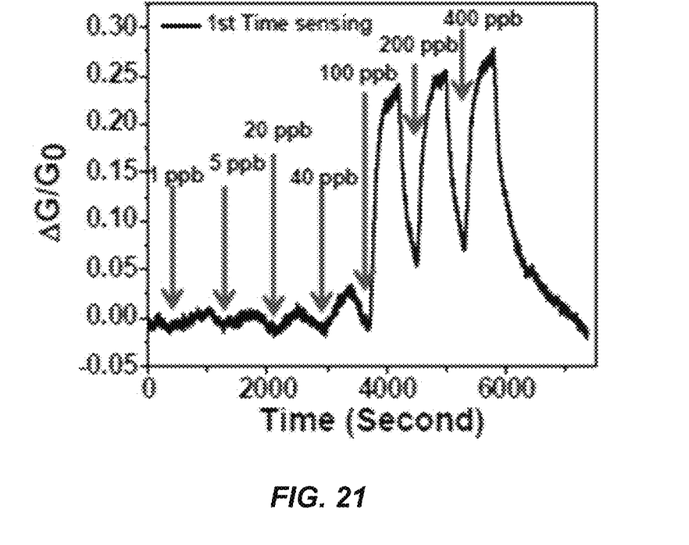
FIG. 21 depicts the relative conductance change ($\Delta G/G_0$) vs. time in seconds for a multilayer BP sensor for a first time sensing.
Figure 22:
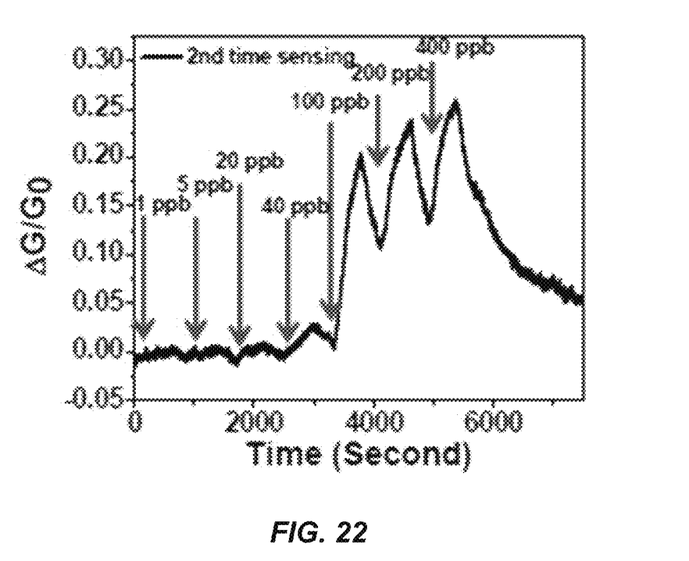
FIG. 22 depicts the relative conductance change ($\Delta G/G_0$) vs. time in seconds for a multilayer BP sensor in response to various concentrations of $NO_2$.

(where C is the concentration in ppb). The fitting further confirms that charge transfer is the sensing mechanism for $NO_2$ sensing in the multilayer BP sensor 10. Moreover, repeated sensing experiments revealed very similar sensing performances of the same BP sensor 10 suggesting a stable performance over the timeframe of the experiment (see FIGS. 21-22). It should be noted that the BP sensor 10 is not specifically selective to $NO_2$. To improve the selectivity of the BP sensor to $NO_2$, further efforts could be applied to modify the BP surface or sensor structure to be selective to a specific chemical species.

Figure 9:
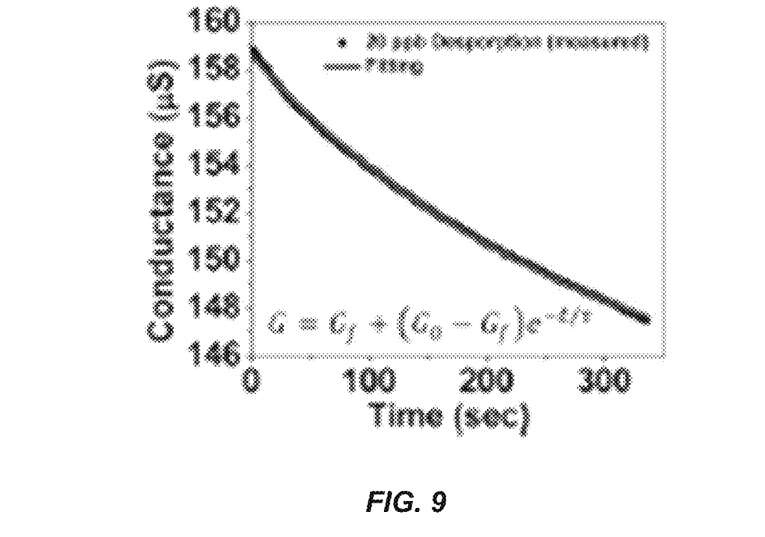
FIG. 9 depicts the measured time-dependent conductance change of a multilayer BP FET (black) flushed with argon after being exposed to 20 ppb $NO_2$.
Figure 10:
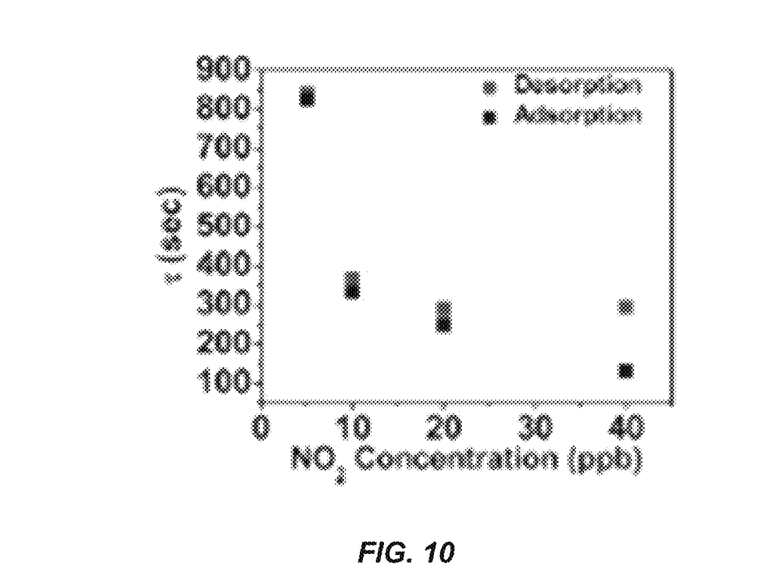
FIG. 10 depicts the rate constants ($\tau$) vs. different concentrations of $NO_2$.

One can define the BP sensor 10 response time as the time required to change the conductance after introducing either $NO_2$ (conductance increase) or argon (conductance decrease) in a specific range by 90%. Accordingly, the inventors calculated the response time of the BP sensor 10, in one implementation, to be in the range of ~280-350 seconds for different concentrations. This value is an indication of the rate the molecules are adsorbed on BP surface and it is comparable to other reports using other 2D materials, such as $MoS_2$ as gas sensors. To further analyze the adsorption and desorption of $NO_2$ molecules on BP, one can extract the absorption/desorption rate constants (τ) of the multilayer BP device. The first order rate equation is of the form:

$$G=G_f+(G_0-G_f)e^{-t/\tau}, \quad \text{(Eq. 2)}$$

where G is the instantaneous conductance, $G_f$ is the final conductance after the end of an adsorption/desorption period, $G_0$ is the initial conductance before an adsorption/desorption period, and t is the time. FIG. 9, shows the measured conductance decrease associated with $NO_2$ desorption and the fitted curve when the BP FET 10 is flushed with argon after being in a 20 ppb $NO_2$ environment. The measured and fitted curves show a nearly perfect agreement with a fitting error of ~1.5%. This agreement suggests that there is only one time constant, and therefore, only one mechanism associated with $NO_2$ molecular adsorption/desorption in the experiment. FIG. 10 plots the adsorption and desorption rate constants (τ) vs. different concentrations of $NO_2$. The extracted τ values varied from ~130 sec for a concentration of 5 ppb to ~840 sec for a concentration of 40 ppb. It can be observed that τ, which is a metric for how fast the $NO_2$ adsorption/desorption process is, decreases as the gas concentration increases and saturates at high concentrations.

The surprisingly high sensitivity of a thick (e.g., approximately 55 nm) multilayer BP flake compared to other multilayer 2D materials such as $MoS_2$ is worth noting. For instance, He et al. observed a ~1% change in $\Delta G/G_0$ when exposing an 18 nm $MoS_2$ flake to 1200 ppb $NO_2$, while the inventors observed a 2.9% change in $\Delta G/G_0$ when exposing a 55 nm BP flake to 5 ppb $NO_2$ (240 times lower in concentration). This difference in response of multilayer samples is potentially material dependent. As was mentioned earlier, the high adsorption energies of NO₂ to BP is one reason causing the high sensitivity of inventors' BP gas sensor 10. Additionally, it was theoretically predicted and experimentally observed that BP layers have less out-of-plain conductance than other 2D materials, such as graphene and MoS₂. This low conductance in the out-of-plane direction in BP compared to the in-plane conductance may explain the observed high sensitivity. Since only the top most BP layer and edges are exposed to NO₂ during sensing, and since the metal contact to the multilayer BP flake is mostly to the top layer, the transport and doping of the top layers may dominantly control the conductance of the device because of the low conductance in the out-of-plane direction.

Figure 19:
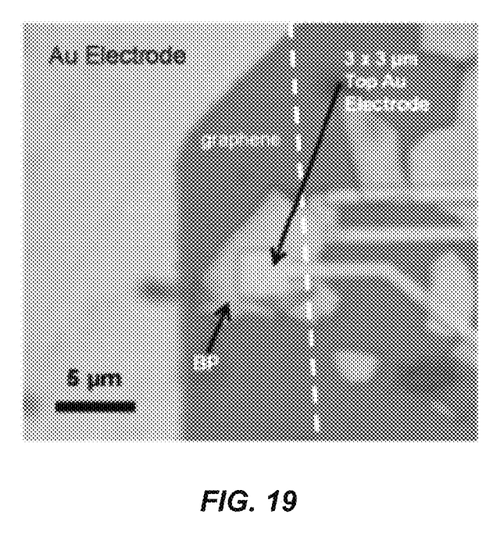
FIG. 19 depicts an optical microscope image of a vertical FET comprised of a bottom monolayer CVD graphene electrode/BP/top (Ti/Au) electrode with a $P^{++}$ Si/300 nm $SiO_2$ back gated structure.
Figure 20:
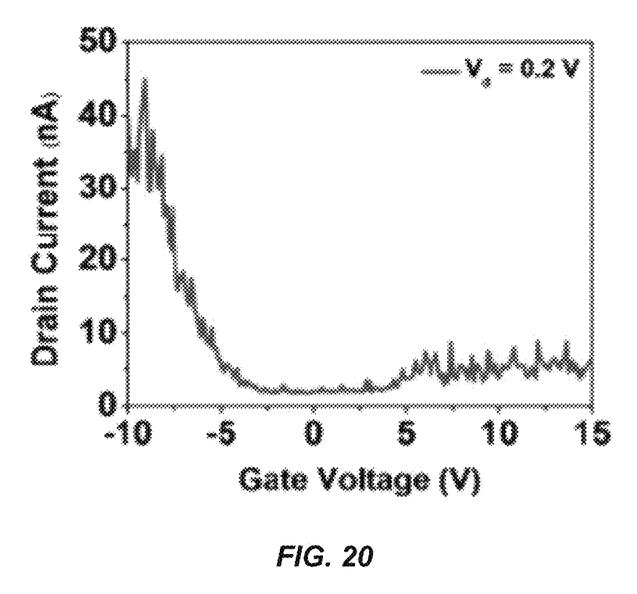
FIG. 20 depicts the $I_d$-$V_G$ curve for the device in FIG. 19.

To further explore the conductance of the out-of-plane direction in BP, the inventors fabricated a vertical structure comprised of a monolayer graphene bottom contact to multilayer BP and a 0.5 nm Ti/50 nm Au top contact (see FIGS. 19 and 20). It can be observed that the ON current value in the vertical BP transistor structure (see FIGS. 19 and 20) is approximately two orders of magnitude lower than the traditional lateral transport FET structure (i.e. 10 μA for $V_d$=0.05V in lateral FET compared to 20-100 nA for $V_d$=0.1 V in vertical FET). Moreover, comparing to a vertical MoS₂ with flake thicknesses in the same range and similar device structure, BP vertical FET structure revealed a vertical current density of 0.5-2.4 A/cm² at $V_d$=0.2 V (see FIGS. 19 and 20), while MoS₂ at the same $V_d$ exhibited a current density of ~800 A/cm². This notably large difference further supports the explanation and hypothesis about the observed high sensitivity in multilayer BP sensors compared to its other 2D counterparts.

Figure 11:
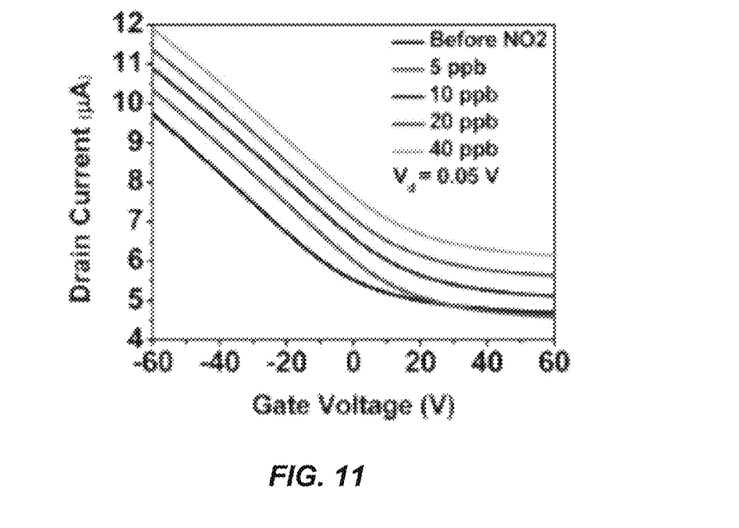
FIG. 11 depicts the $I_d$-$V_g$ curves of multilayer BP FET under different concentrations of $NO_2$.
Figure 12:
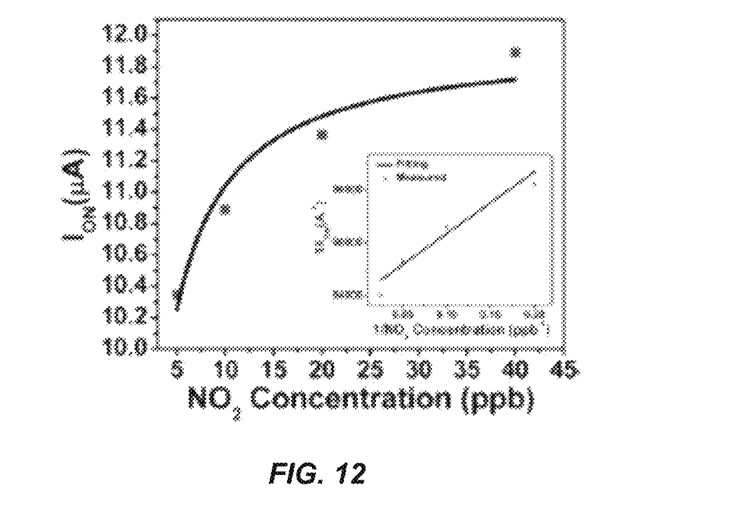
FIG. 12 depicts the measured $I_{ON}$ vs. $NO_2$ concentration (red) and the corresponding fitted Langmuir isotherm (black).
Figure 13:
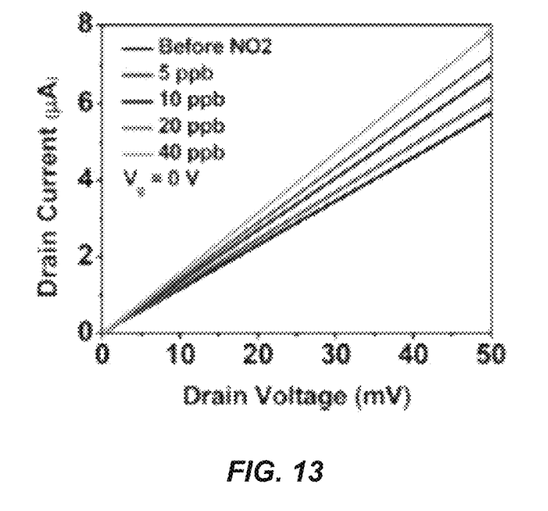
FIG. 13 depicts the $I_d$-$V_d$ curves of multilayer BP FET at different concentrations of $NO_2$.
Figure 14:
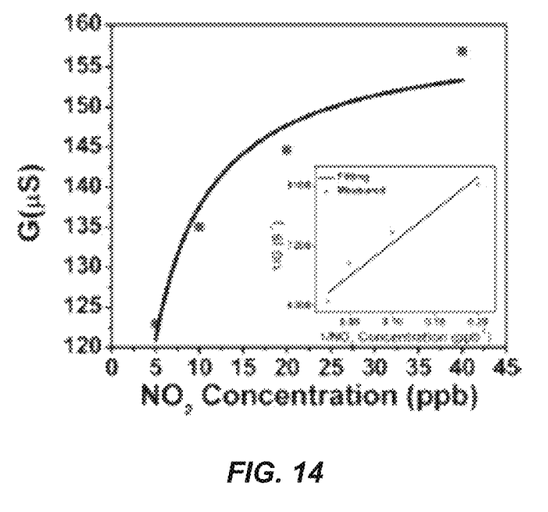
FIG. 14 depicts the measured G vs. $NO_2$ concentration (red) and the corresponding fitted Langmuir isotherm (black).

The inventors further characterize the electronic properties of the multilayer BP FET 10 via observing the change in $I_d$-$V_d$ and $I_d$-$V_g$ curves after exposing the device to different concentrations. First, the device was flushed with argon to clear the system from any contaminants or residual gas species. Then the device was exposed to a specific NO₂ concentration for 500 sec. Subsequently, measurements of $I_d$-$V_d$ and $I_d$-$V_g$ curves were recorded while the device is still exposed to NO₂. Afterwards, the device was flushed with argon for 300 sec before exposing the device to a new concentration of NO₂. FIG. 11 shows the $I_d$-$V_g$ curves of the BP device under different concentrations. An upshift in the curves with increasing NO₂ concentrations associated with extra hole doping was observed. FIG. 12 plots the on current ($I_{ON}$) (defined as current at $V_g$=−60 V) extracted from FIG. 11 vs. the concentration of NO₂ the BP device was exposed to. The measured data points reveal a saturation behavior at higher concentrations and follow the Langmuir Isotherm with equation:

$$I_{ON} = \frac{1.19 \times 10^{-5}}{1 + \frac{0.836}{C(ppb)}}(A), \qquad (Eq. 3)$$

which further supports that charge transfer is the main mechanism for the BP FET sensor 10. The inset of FIG. 12 shows that 1/$I_{ON}$ vs. 1/C(ppb) have a linear relationship, which is another representation of the Langmuir Isotherm in FIG. 12. $I_d$-$V_d$ curves at different concentrations of NO₂ are plotted in FIG. 13. As can be seen, the conductance increases monotonically with increasing NO₂ concentrations. Moreover, the $I_d$-$V_d$ curves maintain their linearity with various NO₂ concentrations indicating minimal effect of Schottky barrier modulation induced by NO₂ exposure under the conditions used in the experiment. FIG. 14 shows the conductance (G) of the inventors' BP sensor extracted from FIG. 13 vs. the concentration of NO₂. The fitted Langmuir Isotherm equation is:

$$G = \frac{1.6 \times 10^{-4}}{1 + \frac{1.59}{C(ppb)}}(S), \qquad (Eq. 4)$$

which agrees with the measured data points. Similar to FIG. 12, the inset of FIG. 14 shows a linear dependence of 1/G vs. 1/C(ppb) which agrees with the Langmuir Isotherm fitting.

BP Synthesis:

The inventors synthesized BP samples from red phosphorus (Chempur, 99.999+%) and tin/tin (IV) iodide (Sn/SnI₄=10/5 mg per 250 mg batch) in evacuated (p<10⁻³ mbar) silica ampoules according to literature procedures. Subsequently, the temperature of the starting materials was raised to 650° C. in a period of 8 hours and that temperature was held for 5 hours. Then, the oven chamber was cooled down to 550° C. in a period of 7.5 hours and was kept at that temperature for 6 hours. Eventually, the mixture was cooled to room temperature.

BP Device Fabrication:

BP flakes were exfoliated using a commercial tape on a P++Si/300 nm SiO₂ substrate with alignment marks patterned. After the flakes were located using optical microscopy, electron beam lithography (EBL) defined electrodes were patterned on the target BP flake. Subsequently, electron beam evaporation of 0.5 nm Ti as an adhesion layer and then 50 nm thick Au layer for contacts were carried out. Then, the sample was soaked in acetone for ~30 mins to do metal lift-off Afterwards, the devices were manually bonded using indium wire bonds after mounting the substrate on a chip carrier. Finally, devices were loaded inside the gas sensing chamber and measurements were recorded.

NO₂ Gas Sensing:

Gas sensing was carried out by exposing the BP FET device to NO₂ gas diluted in argon in a closed chamber. Concentrations of NO₂ were adjusted by changing the flow rates of both gases while keeping the total flow rate constant. For each curve, the device was exposed to the desired concentration for 500 sec and then flushed with argon for 300 sec. Similar procedures were followed to measure $I_d$-$V_d$ and $I_d$-$V_g$ for BP devices.

Accordingly, the invention provides a new and useful black phosphorus gas sensor. Various features and advantages of the invention are set forth in the following claims.

What is claimed is:

1. A black phosphorus gas sensor having repeatable sensing performance, the sensor comprising:
a substrate;
a black phosphorus flake supported by the substrate, the black phosphorus flake having a thickness greater than 15 nanometers; and
a plurality of electrical contacts supported by the substrate and coupled to the black phosphorus flake,
wherein the substrate, black phosphorus flake, and plurality of electrical contacts form a field effect transistor;
wherein the black phosphorus flake responds to a gas, resulting in the conduction of the field effect transistor based on the concentration of the gas; and wherein the plurality of electrical contacts includes respective Ti/Au contacts.

2. The sensor of claim 1, wherein the gas includes nitrogen dioxide.

3. The sensor of claim 2, wherein the sensor permits conduction when the nitrogen dioxide concentration has a concentration greater than 53 parts per billion.

4. The sensor of claim 2, wherein the sensor permits conduction when the nitrogen dioxide concentration has a concentration greater than 40 parts per billion.

5. The sensor of claim 2, wherein the sensor permits conduction when the nitrogen dioxide concentration has a concentration greater than 5 parts per billion.

6. The sensor of claim 1, wherein the substrate includes a $P^{2+}$ Si/SiO$_2$ substrate.

7. The sensor of claim 1, wherein the black phosphorus flake is synthesized from red phosphorus and tin/tin(iV) iodide.

8. The sensor of claim 1, wherein the black phosphorus flake has a thickness greater than 50 nanometers.

9. The sensor of claim 1, wherein the black phosphorus flake has a thickness approximately 55 nanometers.

10. A method of manufacturing a black phosphorus gas sensor, the method comprising
    synthesizing black phosphorus;
    exfoliating the black phosphorus to result in a black phosphorus flake;
    disposing the black phosphorus flake a substrate; and
    patterning a plurality of electrodes on the substrate and coupling with the black phosphorus flake.

11. A method of sensing a gas with the black phosphorus gas sensor of claim 1, the method comprising:
    providing the black phosphorus gas sensor at a location;
    exposing the black phosphorus gas sensor to a gas;
    conducting a current from a first electrode to a second electrode of the plurality of electrodes and through the black phosphorus flake, the conducting being based on the concentration of the gas.

12. The method of claim 11, wherein the gas includes nitrogen dioxide.

13. The method of claim 11, wherein the conducting a current occurs when the nitrogen dioxide concentration has a concentration greater than 53 parts per billion.

14. The method of claim 11, wherein the conducting a current occurs when the nitrogen dioxide concentration has a concentration greater than 40 parts per billion.

15. The method of claim 11, wherein the conducting a current occurs when the nitrogen dioxide concentration has a concentration greater than 5 parts per billion.

16. The method of claim 11, wherein the black phosphorus flake has a thickness greater than 50 nanometers.

17. The method of claim 11, wherein the black phosphorus flake has a thickness approximately 55 nanometers.

* * * * *